United States Patent [19]

Helting et al.

[11] 4,271,147
[45] Jun. 2, 1981

[54] PROCESS FOR THE ISOLATION OF MEMBRANE PROTEINS FROM *NEISSERIA MENINGITIDIS* AND VACCINES CONTAINING SAME

[75] Inventors: Torsten B. Helting, Perchtoldsdorf, Austria; Gerhard Guthöhrlein, Marburg an der Lahn, Fed. Rep. of Germany

[73] Assignee: Behringwerke Aktiengesellschaft, Marburg an der Lahn, Fed. Rep. of Germany

[21] Appl. No.: 110,945

[22] Filed: Jan. 10, 1980

[51] Int. Cl.³ ............... A61K 39/095; C07C 103/52
[52] U.S. Cl. .................................. 424/92; 424/88; 260/112 R
[58] Field of Search ............... 424/88, 92; 260/112 R

[56] References Cited
PUBLICATIONS

Chemical Abstracts, vol. 81, Abstract No. 89474a, Frasch et al., "Outer membrane protein of *Neisseria meningitidis*", J. Exp. Med., 1974.
Chemical Abstracts, vol. 91, Abstract No. 191152n, Hoff et al., "Outer membrane antigens of *Neisseria meningitidis* group B serotype 2 studied by crossed immunoelectrophoresis, Infect. Immunity, 1979.
Frasch, C. et al., J. of Bact., vol. 127, pp. 973–81, 1976.

*Primary Examiner*—Delbert R. Phillips
*Assistant Examiner*—Blondel Hazel
*Attorney, Agent, or Firm*—Curtis, Morris & Safford

[57] ABSTRACT

Membrane proteins are isolated from *Neisseria meningitidis* by direct treatment of the cells with a detergent. The membrane proteins can be worked up into a vaccine.

7 Claims, No Drawings

PROCESS FOR THE ISOLATION OF MEMBRANE PROTEINS FROM *NEISSERIA MENINGITIDIS* AND VACCINES CONTAINING SAME

This invention relates to an improved process for the isolation of membrane proteins from *Neisseria meningitidis* and to vaccines containing the said membrane proteins.

The causative organism of Meningitis cerebrospinalis epidemica is *Neisseria meningitidis*, also called meningococcus. Meningitis is spread by droplet infection and occurs mostly in children and people in mass quarters. It is, therefore, desirable to immunize the endangered groups.

According to the present knowledge, the major outer membrane protein of *Neisseria meningitidis* is in a position to induce bactericidal antibodies. These antibodies offer a type-specific protection against the disease. Other components of Neisseria, especially the capsular polysaccharides of Neisseria groups A and C, may ensure a group specific protection, but they do not induce an effective protection against Neisseria group B. Moreover, it has not yet been ascertained whether the capsular polysaccharide of group B is in a position to induce such protection. Therefore, the membrane proteins of *Neisseria meningitidis* group B are of special interest.

For the manufacture of a vaccine, the major membrane protein from *Neisseria meningitidis* group B must be isolated in a sufficient amount. The process described by Frasch in J. Bact. 127, 973–981 (1976) yields a useful preparation. The yield obtained in this process is, however, at the lower, economically acceptable limit. The essential features of the Frasch process are washing the cells of *Neisseria meningitidis* with salt solutions ($CaCl_2$ or $LiCl$ solutions) and then treating the extract with deoxycholate. As mentioned above, rather poor yields are obtained.

It has now been found, surprisingly, that the yield can be considerably improved by subjecting the bacterial cell mass to a direct treatment with detergents. The material obtained by the process according to the invention does not differ noticeably from the membrane protein preparations according to Frasch. It has the same electrophoretic properties in SDS-containing buffer solutions. Its endotoxin content can be compared with that of the Frasch material as well as its ability to induce protective antibodies in animals.

It is, therefore, the object of the present invention to provide a process for the isolation of membrane protein from *Neisseria meningitidis*, especially membrane proteins of group B, which comprises contacting the organisms with the aqueous solution of a detergent in a concentration of from 0.1 to 2% and allowing the mixture to stand for 15 minutes to 24 hours, optionally with agitation, separating the extract from the bacteria residue and further purifying the extract, if desired.

The preferred detergent is deoxycholate, especially its readily water-soluble sodium salt. The concentration of the detergent of 0.1 to 2% is related to the weight of the detergent in grams per volume in milliliters. The proportion of moist bacteria mass to detergent solution is preferably in the range of from 1:3 to 1:20, more preferably 1:5 (w/v).

When sodium deoxycholate is used as the detergent, its concentration is in the range of from 0.3 to 1% in an aqueous solution. Suitable aqueous solutions are mainly the buffer solutions generally used in biochemistry and microbiology.

As the starting material, *Neisseria meningitidis* is grown in usual manner and the cell mass is separated from the supernatant of the culture medium, preferably by centrifugation. The residue of centrifugation is suspended in the detergent-containing solution and allowed to stand for some time. Next, the extract is separated from the cell residue. This is preferably also done by centrifugation.

The temperature at which the extraction is carried out is limited, the lower limit is the freezing point of the solutions used and the upper limit is determined by the loss of immunogeneity of the membrane proteins by heat denaturation. It is, therefore, advisable to operate at a temperature between room temperature and approximately 60° C.

If desired, the extract can be further purified. To this end, the residue obtained by ultracentrifugation is subjected again to an extraction with the detergent-containing solution and, if necessary, this extraction is repeated once more. In each operation, the supernatant of the ultracentrifugation is rejected and the residue is suspended in the detergent-containing aqueous solution.

An enrichment or purification is likewise possible using precipitating agents, as is usual in biochemistry for proteins and corresponding antigens. The *Neisseria meningitidis* antigen can be precipitated, for example, by adding 4 parts by volume of ethanol and the precipitate can be taken up again in aqueous solution.

The *Neisseria meningitidis* antigen filtered under sterile conditions and optionally lyophilized is capable of inducing protective antibodies against the causative organism.

The antigen can be admixed with adjuvants, stabilizers, fillers and similar substances as used in the preparation of vaccines.

The membrane proteins display an immunogenic effect. It is, therefore, another object of the present invention to provide a vaccine containing the membrane proteins prepared in accordance with the process of the invention in an amount sufficient to induce an immunizing effect. The vaccine can be administered in a dosage of from about 10 to 200 μg per dose.

The following examples illustrate the invention.

EXAMPLE 1

300 g (wet weight) of sedimented *Neisseria meningitidis* group B organisms, (strain 986), were resuspended in 1,500 ml of sodium deoxycholate solution (0.5% of sodium deoxycholate in 0.01 M tris-HCl, pH 8.5, 0.01 M EDTA) which had previously been heated to 60° C. and the suspension was kept for 15 minutes in a water bath (56° C.). The bacterial cell mass was then separated by centrifugation (Sorvall GSA Rotor, 10,000 rpm). The residue was again treated as described above for 15 minutes with sodium deoxycholate solution. The suspension was centrifuged and the second supernatant was combined with the first one. The combined supernatants were then centrifuged in a Beckmann L 75 centrifuge at 40,000 rpm for 60 minutes in a 45 Ti Rotor. The sediment was suspended in 150 ml of sodium deoxycholate solution and stirred overnight at 4° C.

For further purification, the suspension was heated on the following day in a water bath (56° C., 15 minutes), centrifuged again in the ultracentrifuge as used above (Rotor 45 Ti, 40,000 rpm, 60 minutes) and the sediment was resuspended in 150 ml of sodium deoxycholate solution. For resuspension, an Ultrasonic Cleaner of Laboratory Supplies Co., Inc., Hickville N.Y., USA was used. Aliquots of 50 ml each were treated for 3 minutes with ultrasonic waves and then combined. Particulate material was separated by another centrifugation (Sorvall, SS-34 Rotor, 20,000 rpm, 20 minutes) and the supernatant was filtered. The membrane protein was precipitated under sterile conditions by the addition of 600 ml of 96% ethanol and allowed to stand for 60 minutes. The precipitate was separated by centrifugation (Sorvall, GSA Rotor), washed once with 100 ml of ethanol, taken up under sterile conditions in 150 ml of 5% raffinose and stirred overnight at 4° C.

The optical density (O.D.) of the material (280 nm) was determined and adjusted to $O.D._{280} = 1.2$ by adding 0.5% raffinose. The concentrate obtained in this manner was worked up to a vaccine in a usual manner.

For the determination of the optical density an aliquot portion was taken under sterile conditions, 1 part by volume of trichloroacetic acid (TCA) of 10% strength was added to bring about precipitation, the precipitate was washed in 5% TCA and taken up in 1 M KOH.

EXAMPLE 2

50 g of sedimented organisms were worked up as described in Example 1 with the exception that a solution of 0.1% of sodium deoxycholate was used instead of a 0.5% sodium deoxycholate solution. 0.8 mg/g of membrane proteins of cell mass was obtained, while the yield in Example 1 was 2.3 mg/g.

EXAMPLE 3

50 g of cells were worked up as described in Example 1, but a solution with 2.0% of sodium deoxycholate was used instead of the 0.5% sodium deoxycholate solution. 2.2 mg of membrane proteins were obtained per gram of germs, while the yield in Example 1 was 2.3 mg/g.

EXAMPLE 4

50 g of cells were worked up as described in Example 1, but instead of 0.5% sodium deoxycholate in 0.01 M tris-HCl-0.01 M EDTA, 0.5% sodium deoxycholate was used in (a) 0.1 M phosphate buffer, pH 7.8, (b) in Hepes buffer (0.1 M, pH 7.8) and (c) in 0.1 M sodium carbonate buffer, pH 8.5. The yields obtained varied between 1.8 and 2.5 mg of membrane proteins per gram.

EXAMPLE 5

The extraction described in Example 1 was carried out with other detergents. The yields are listed in the following table.

| Detergent | concentration | yield (mg/g wet weight) |
|---|---|---|
| urea | 4 M | 1.2 |
| Emulphogen$^{(R)}$ 1 % | 1 % | 1.3 |
| Tween 20$^{(R)}$ | 1 % | 2.6 |
| Triton × 100$^{(R)}$ | 1 % | 2.7 |

What is claimed is:

1. A method for isolating membrane proteins from *Neisseria meningitidis*, which method comprises extracting *Neisseria meningitidis* organisms at least once for 15 minutes to 24 hours with an aqueous solution containing a detergent in a concentration from 0.1 to 2 percent weight/volume and then separating and recovering the supernatant extract which now contains said membrane proteins.

2. The method as in claim 1 wherein said organisms and aqueous solution are agitated during the extraction.

3. The method as in claim 1 wherein said *Neisseria meningitidis* organisms are a group B strain.

4. The method as in claim 1 wherein said detergent is deoxycholate.

5. The method as in claim 1 wherein said detergent is Tween 20.

6. The method as in claim 1 wherein said membrane protein is further purified by precipitating it from the supernatant extract and then redissolving it in an aqueous medium.

7. A vaccine against meningitis cerebrospinalis epidemica, said vaccine comprising an immunologically effective amount of membrane proteins isolated by the method of claim 1.

* * * * *